(12) United States Patent
Font Santafe

(10) Patent No.: US 10,801,006 B2
(45) Date of Patent: Oct. 13, 2020

(54) DEVICE FOR OBTAINING IMAGES OF BACTERIAL CULTURES IN A DISH

(71) Applicant: IUL, S.A., Barcelona (ES)

(72) Inventor: Vicente Font Santafe, Barcelona (ES)

(73) Assignee: IUL, S.A., Barcelona (ES)

(*) Notice: Subject to any disclaimer, the term of this patent is extended or adjusted under 35 U.S.C. 154(b) by 286 days.

(21) Appl. No.: 15/761,857

(22) PCT Filed: Sep. 21, 2016

(86) PCT No.: PCT/IB2016/001345
§ 371 (c)(1),
(2) Date: Mar. 21, 2018

(87) PCT Pub. No.: WO2017/051238
PCT Pub. Date: Mar. 30, 2017

(65) Prior Publication Data
US 2018/0258383 A1    Sep. 13, 2018

(30) Foreign Application Priority Data

Sep. 24, 2015 (EP) .................................. 15380042

(51) Int. Cl.
*C12M 1/34* (2006.01)
*G01N 15/02* (2006.01)
*G01N 15/14* (2006.01)
*G01N 21/01* (2006.01)

(52) U.S. Cl.
CPC .............. *C12M 41/36* (2013.01); *C12M 1/34* (2013.01); *G01N 15/0205* (2013.01); *G01N 15/14* (2013.01); *G01N 21/01* (2013.01); *G01N 2021/0112* (2013.01);
(Continued)

(58) Field of Classification Search
CPC ......... C12M 41/36; C12M 1/34; G01N 21/01; G01N 21/34; G01N 15/0205; G01N 15/14; G01N 2201/06; G01N 2201/0492; G01N 2201/021; G01N 2021/0125;
(Continued)

(56) References Cited

U.S. PATENT DOCUMENTS 5,545,561 A * 8/1996 Lleonart Aliberas ........................ C12M 41/36
211/153
2015/0355101 A1* 12/2015 Sun ...................... H04N 13/254
348/46

FOREIGN PATENT DOCUMENTS

| EP | 0625569 | 11/1994 |
| EP | 1686368 | 8/2006 |
| EP | 2236596 | 10/2010 |

(Continued)

OTHER PUBLICATIONS

International Search Report and written opinion dated Dec. 13, 2016 for PCT/IB2016/001345.

*Primary Examiner* — Michael L Hobbs
(74) *Attorney, Agent, or Firm* — Silvia Salvadori

(57) ABSTRACT

The present invention relates to a device for obtaining images of bacterial cultures in a dish. The proposed device includes a support for a culture dish to be analyzed surrounded by an annular light emitting source facing an image capturing device and a non-reflective surface which, in conjunction with a reflective surface arranged in the periphery of the support, form a preferably spherical-shaped contrast observation chamber, providing a glare- and reflection-free, uniform tangent illumination of the support.

17 Claims, 6 Drawing Sheets

(52) U.S. Cl.
CPC ............... *G01N 2021/0125* (2013.01); *G01N 2201/021* (2013.01); *G01N 2201/0492* (2013.01); *G01N 2201/06* (2013.01)

(58) Field of Classification Search
CPC .. G01N 2021/0112; F21L 19/006; F21V 3/00; F21V 3/02; F21V 15/00
See application file for complete search history.

(56) References Cited

FOREIGN PATENT DOCUMENTS

| | | | |
|---|---|---|---|
| WO | WO-2012116190 A1 * | 8/2012 | ............ F16F 9/3481 |
| WO | 2014167566 | 10/2014 | |

* cited by examiner

DEVICE FOR OBTAINING IMAGES OF BACTERIAL CULTURES IN A DISH

RELATED APPLICATIONS

This application is a US national phase application of International application number PCT/IB2016/001345, filed 21 Sep. 2016, which designates the US and claims priority to European application EP 15380042.0 filed 24 Sep. 2015, the contents of each of which are hereby incorporated by reference as if set forth in their entireties.

FIELD OF THE ART

The present invention relates to the field of devices providing a contrast chamber for observing bacterial colonies that develop in plates on which the culture is carried out, with respect to the culture medium of said bacterial colonies.

As is well known, bacterial cultures are carried out for the purpose of determining the number and type of bacteria present, for example, in a food, pharmaceutical product, etc.

Bacterial culture is carried out on plates known by the name of PETRI plates on which there is deposited a base product consisting of a gelled agar-agar solution which is the food for the bacteria, on which an extract of the product to be analyzed is deposited, the plate being subsequently deposited in an oven to favor bacterial growth, different colonies being created from each microorganism present in the extract of the product to be analyzed.

The purpose of the mentioned contrast observation chamber provided by the invention is to acquire images of said bacterial colonies which enable, through automatic processing of said images, an automatic count to determine the number of developed bacterial colonies, an obtained image also being able to be shown on a display in which the bacteria are depicted such that they are duly separated from one another, particularly by means of color or measurements of the zones of inhibition. Said images will be acquired by means of an electronic image capturing device, particularly a high-resolution digital photographic camera, duly focused on the zone in which the plates, for example, PETRI dishes, are deposited.

STATE OF THE ART

Patent document EP 0625569 describes a device with a contrast chamber for spotlighting bacterial colonies with respect to the culture medium thereof, wherein the plates are arranged inside the contrast chamber and covered by means of a dark opaque disk, opposite a reading head, located below the plate, and the latter is illuminated from several planes that are not parallel to the capturing plane of said reading head.

Patent document EP 1686368 describes a device similar to the one above wherein the illumination source is formed by a plurality of LED illumination elements arranged in an annular formation directing their beams against a reflective surface, and the reflected light goes through the PETRI plate containing the culture sample to finally arrive at an image capturing device.

A device of the aforementioned type which is referred to as an automatic colony counter marketed under the brand "Petrilyzer" by the company Bioras that works by counting bacterial colonies on PETRI dishes using image analysis is also known in the sector. The device proposes a cylindrical chamber having a groove for placing PETRI dishes on a support and having a superposed and spaced away chamber for acquiring images. The illumination consists of a LED ring located close to the inner cylindrical surface below the transparent support for the PETRI dishes.

None of the mentioned prior art documents disclose the use of an indirect, reflected light hitting the PETRI plates with a uniform and regulated light intensity, which is the objective of the present invention.

BRIEF DESCRIPTION OF THE INVENTION

The present invention relates to a device for obtaining images of bacterial cultures in a dish.

Bacterial cultures carried out on a culture dish usually require counting the bacterial colonies developed on said culture dish. Manual methods or, as described, automatic image recognition systems can be used to carry out said counting, but in both cases it is necessary to obtain an image of the culture dish under optimum illumination conditions, which allow highlighting and distinguishing the colonies from the substrate on which they develop, and from one another, reflections, shadows, irregular illumination, intercalated luminous points or other optical distortion effects which may be caused by an incorrect illumination being prevented.

For this purpose, the present invention proposes a device including:
  a support for culture dishes;
  an annular light emitting source arranged around said support for culture dishes, the light emitted by said source being oriented in a direction not hitting said support for culture dishes;
  a reflective surface arranged facing said light emitting source for reflecting said light towards the support for culture dishes, and
  a centered image capturing device, facing and spaced from said support for culture dishes, for capturing images of a culture dish deposited on said support for culture dishes;

Therefore, the device that has been described includes a support on which the culture dish to be analyzed is placed, said support being located facing an image capturing device intended for obtaining images of the entire culture dish located on said support, or of part of the dish. Said support will usually be a horizontal surface, and said image capturing device will be located in a centered manner above the support, separated from same. It is also contemplated that the support is transparent and the image capturing device is located below said support, observing the dish through same.

An annular light emitting source is arranged around the support, surrounding said support, the emitting source being oriented such that the main flow of emitted light does not hit the support or on a culture dish deposited on said support in this case.

This emitted light is reflected on a reflective surface envisaged for reflecting the light, returning a significant fraction of the light on the culture dish, thereby illuminating it with an indirect, uniform reflected light.

In a novel manner, it is proposed that the mentioned at least one reflective surface, in combination with a non-reflective surface, form a contrast observation chamber in which the culture dishes arranged on the support for culture dishes are confined, the annular light emitting source and the image capturing device being integrated inside said observation chamber, and it is also proposed that said non-reflective surface is arranged in an annular manner around the image capturing device, superposed with respect to the support for culture dishes and facing and spaced from same, said non-reflective surface being provided with a surface finish with an albedo less than 0.4.

The culture dish to be observed would therefore be confined in a contrast observation chamber made up of a non-reflective surface that would be located in a position superposed with respect to the support, approximately facing same, and of a reflective surface surrounding it.

The contrast observation chamber will preferably block external light entering same, thereby preventing possible chromatic distortions, zones with shadow, reflections, etc., due to the incidence of external light.

Furthermore, the position of the non-reflective surface arranged around the image capturing device, and facing and superposed with respect to the support, prevents the occurrence of reflections in the captured images. If said region were reflective, the light beams emitted by the light emitting source would be reflected on said reflective surface and hit a culture dish located on the support with an angle of incidence close to 90°, which may cause it to be reflected again in a direction almost perpendicular to the culture dish towards the image capturing device. Reflection of this type, with an angle of incidence and reflection on the culture dish close to 90°, would generate glare and reflections which may make counting bacterial colonies in the acquired images difficult.

For this reason, it is proposed that the entire surface surrounding the image capturing device is a non-reflective surface, which prevents the light hitting thereon from being reflected towards the culture dish, said problems being avoided. Therefore, all the light hitting the support or on a culture dish arranged on the mentioned support comes from the light reflected on the reflective surface, which is located in the position in which there is no non-reflective surface, i.e., not around the image capturing device, or in a position facing or superposed with respect to the support, said reflective surface therefore being located in a peripheral region with respect to the support, producing side illumination by reflection. As a result of this arrangement, it is assured that the light hitting the culture dish forms an angle considerably less than 90°.

It will be understood in the present document that a non-reflective surface will be any surface having a surface finish with an albedo less than 0.4, i.e., said non-reflective surface will only be capable of returning less than 40% of the incident light energy. Said albedo of the non-reflective surface will preferably be less than 0.2.

Similarly, it will be understood that a reflective surface will be any surface capable of reflecting at least 40% of the incident light, although the albedo of its surface finish being at least 0.6 or 0.8 is considered preferable.

According to another embodiment, it is proposed that the reflective surface and/or the non-reflective surface have the geometry of a spherical portion. In other words, either of or both surfaces have the geometry of a portion of a sphere, which assures a correct and uniform light distribution through the inside of the contrast observation chamber.

Additionally, it is proposed that said reflective surface has at least one of its two poles truncated a diameter greater than the diameter of said annular light emitting source, allowing said reflective surface to surround the light emitting source.

In another embodiment, it is proposed that the non-reflective surface has the geometry of a spherical cap truncated with a diameter greater than the diameter of said annular light emitting source, whereby assuring that there is no reflective surface in the vertical of the light emitting source.

It is also proposed that at least part of the reflective surface, or at least part of the reflective surface together with at least part of the non-reflective surface, is movable from a closed position surrounding said support, in which images of a culture dish can be obtained with optimum illumination conditions, and an open position, in which an access is offered for introducing culture dishes in the observation chamber. Optionally, said movement is performed in a direction perpendicular to the support for culture dishes.

This movement of the entire or part of the reflective surface, accompanied or not accompanied by part of the non-reflective surface, allows opening the contrast observation chamber, which allows introducing, handling or replacing the culture dish, while at the same time provides the possibility of closing said chamber, preventing external light from entering, for obtaining optimum images with a controlled light.

The movable part of the contrast observation chamber is preferably attached to guide means which allow its movement and limit its travel by drive means consisting of a rotor and a connecting rod. The guide means can consist of many different configurations, such as for example, runners and sliding surfaces on which to move them, a cam and a cam follower, one or more shafts inserted in holes, or bars with introduced rings, allowing the relative movement thereof in one direction, etc. Similarly, the drive means can also be of very different type, such as for example, a spindle operated by a motor or a crank, a stressed elastic element which is released causing a movement, a piston, a linear motor, or like in the preferred case which has been described, a connecting rod with an end connected to a rotor which, with its rotation, causes said end to move in a circular path, the opposite end of the connecting rod being able to produce a linear movement. This rotor and connecting rod mechanism, combined with the guide means and connected to the movable part of the contrast observation chamber, can cause the vertical movement thereof between the open and closed positions.

Additionally, the device will be equipped with at least one spring means counteracting the weight of the movable part of the contrast observation chamber in said open position, which allows reducing the efforts made by a motor which will drive the rotor and the connecting rod, likewise allowing said motor to have reduced rated power and size.

According to another embodiment which has been envisaged, the support for culture dishes is transparent, allowing optionally placing below same an alternative light emitting source facing said support, the light of which would go through the support and the culture dish, offering alternative illumination. In this case, the non-reflective surface arranged facing said support would also prevent the light emitted by this alternative light emitting source from being reflected, producing glare on the culture dish.

Additionally, it is envisaged that the non-reflective surface has a size greater than the support for culture dishes, only the mentioned non-reflective surface and the image capturing device being superposed with respect to the support for culture dishes. The non-reflective surface is therefore larger than the support for culture dishes, such that only the non-reflective surface and the image capturing device, which can be, for example, a high-resolution digital photographic camera, are located above said support, vertically superposed with respect to same.

The non-reflective surface preferably has a diameter greater than the annular light emitting source.

The device can also include image processing equipment with a microcontroller running an algorithm for counting bacterial colonies of any color and/or size and/or measuring zones of inhibition of said observed bacterial cultures using said image capturing means.

It will be understood that the present device can also be applied for counting any other type of development of microorganisms, such as microbes, fungi, or the like.

Other features of the invention will be shown in the following detailed description of an embodiment.

BRIEF DESCRIPTION OF THE DRAWINGS

The foregoing and other advantages and features will be better understood based on the following detailed description of an embodiment in reference to the attached drawings which must be interpreted in an illustrative and non-limiting manner, in which.

DETAILED DESCRIPTION OF AN EMBODIMENT

Figure 3:
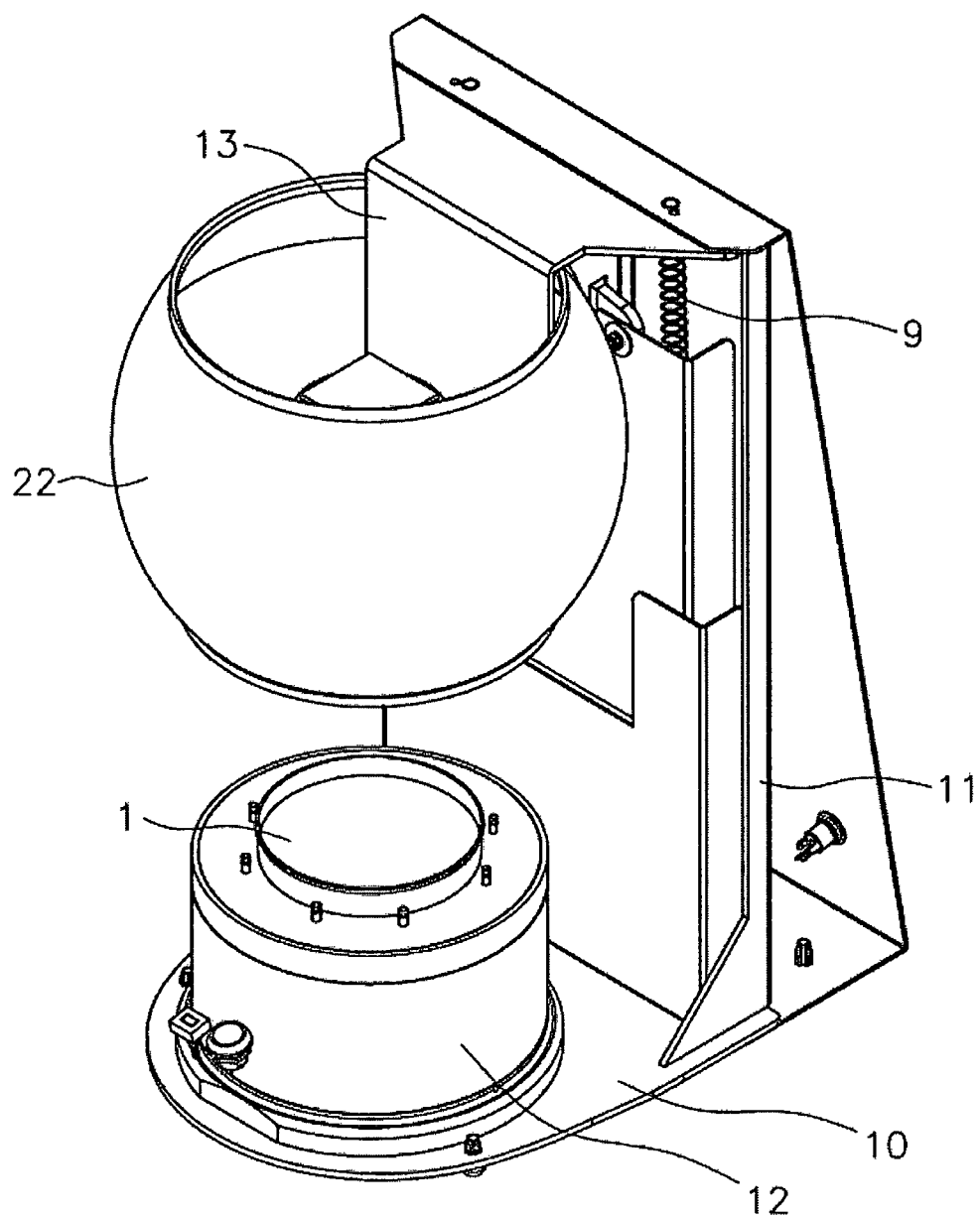
FIG. 3 shows a perspective view of the device shown in FIG. 1, in an open position.

FIGS. 1, 2, 3 and 4 show, in an illustrating and non-limiting manner, an embodiment whereby the device for obtaining images of bacterial cultures in a dish consists of a framework formed by a base 10 and a wall 11 attached to said base 10. A cylindrical pedestal 12 supporting an annular light emitting source 2 formed by a ring of LED lights surrounding the glass support 1 for culture dishes is erected on the base 10, as shown in FIG. 3. Optionally, an alternative light source can be located within the pedestal to illuminate the culture dish through the transparent support.

Figure 1:
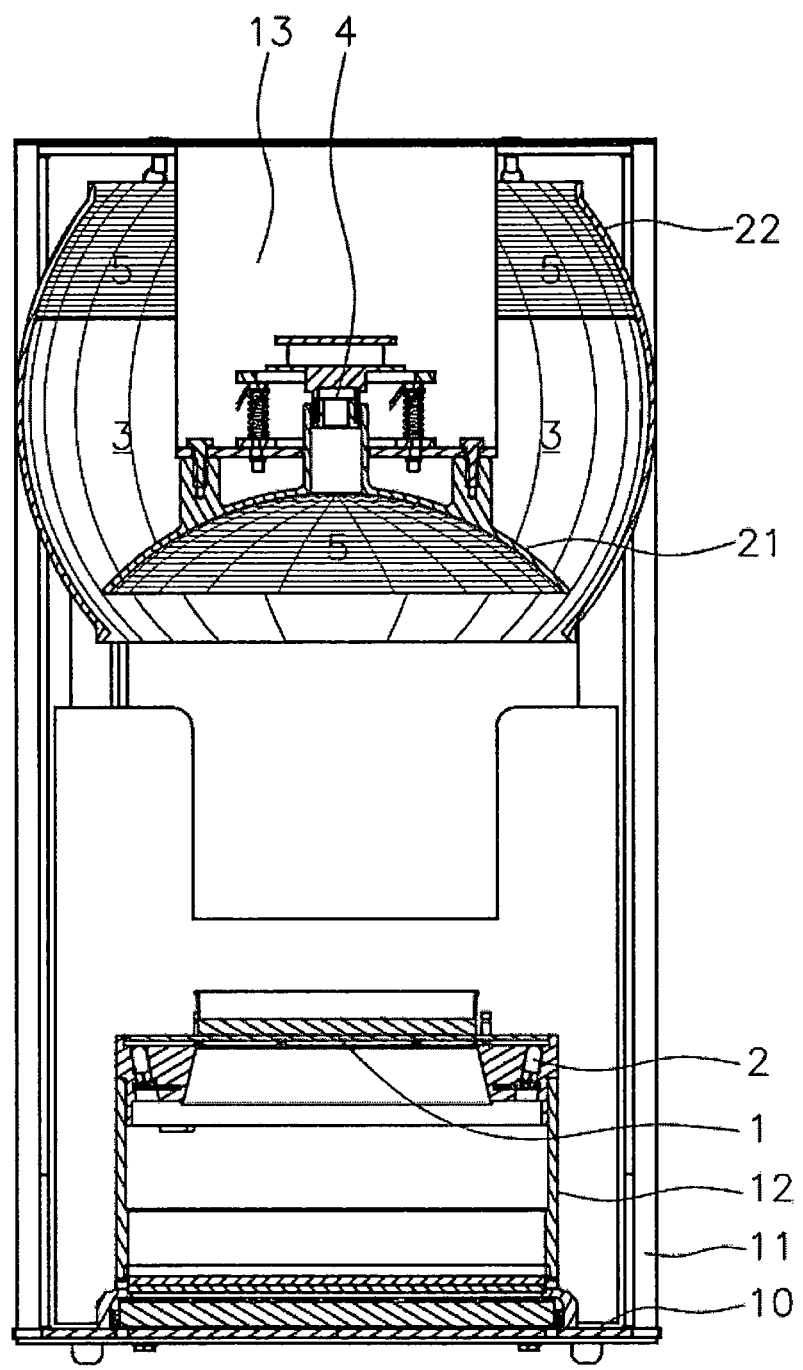
FIG. 1 shows a sectioned view of the device for obtaining images according to an embodiment in which the contrast observation chamber is made up of a first screen in the form of a hollow spherical cap and a second screen in the form of a hollow sphere with its two poles truncated, said contrast observation chamber being in an open position with the second screen raised.
Figure 2:
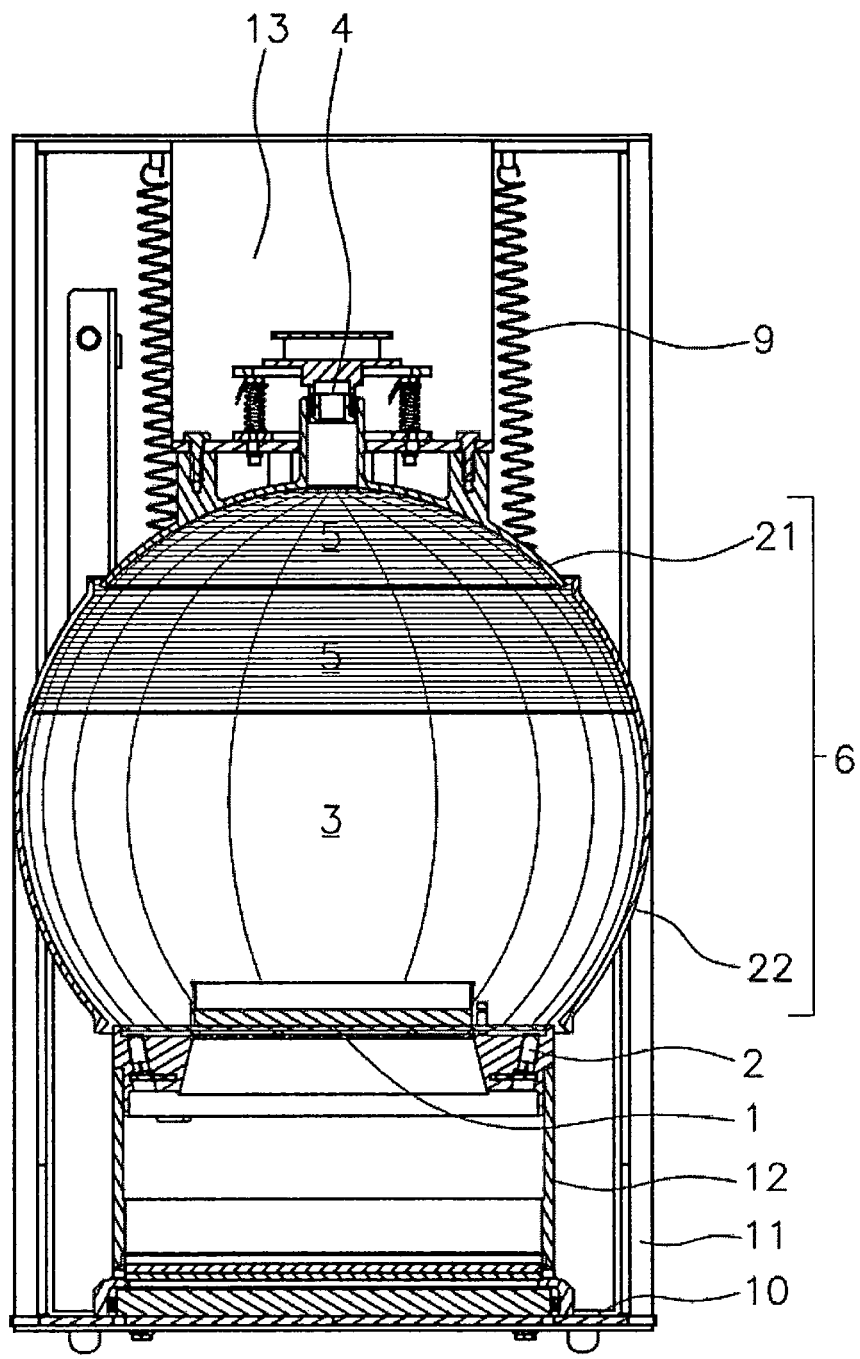
FIG. 2 shows the same view shown in FIG. 1, the contrast observation chamber being in a closed position with the second screen lowered closing said chamber and preventing external light from entering.
Figure 4:
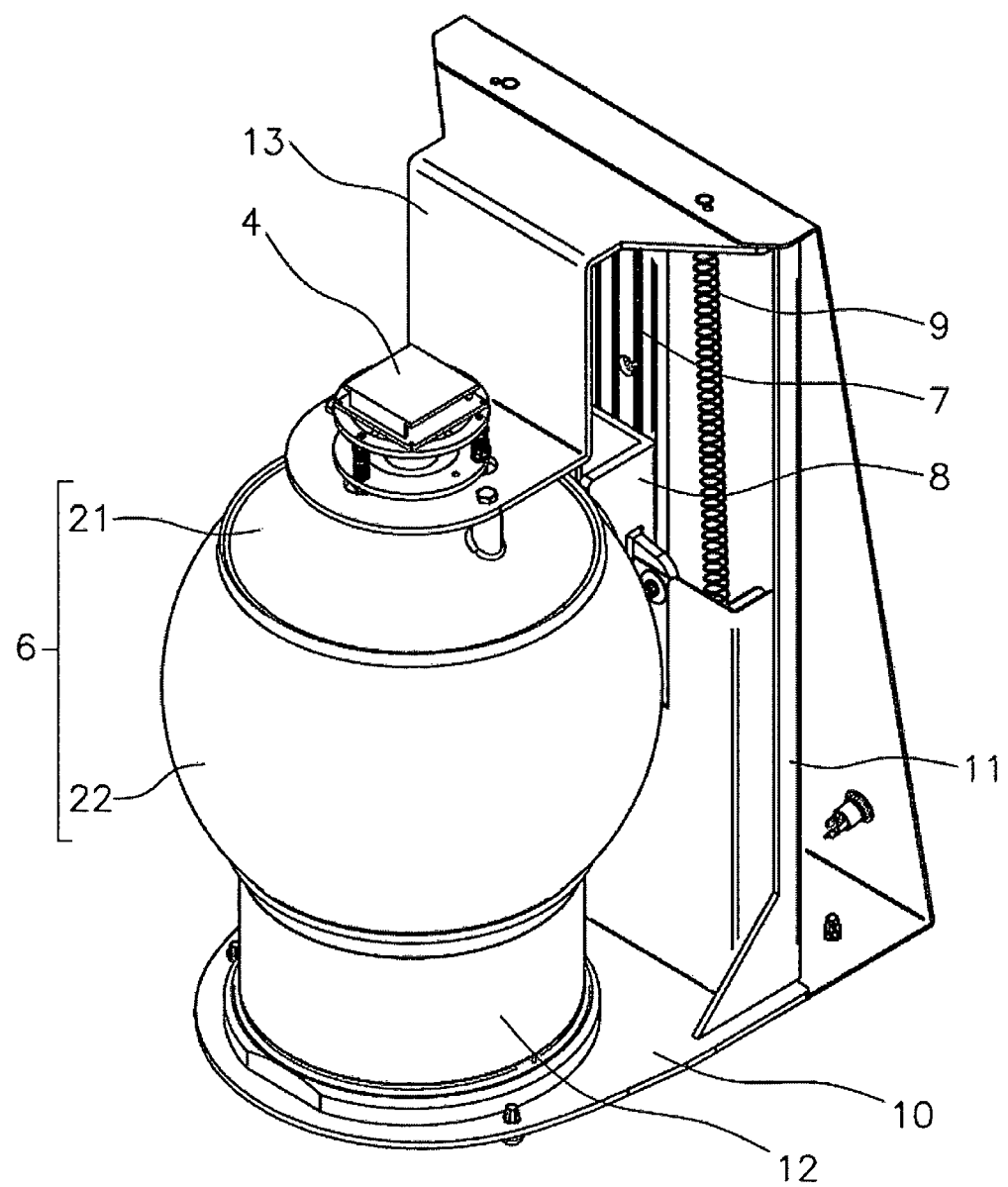
FIG. 4 shows a perspective view of the device shown in FIG. 2, in a closed position.
Figure 5:
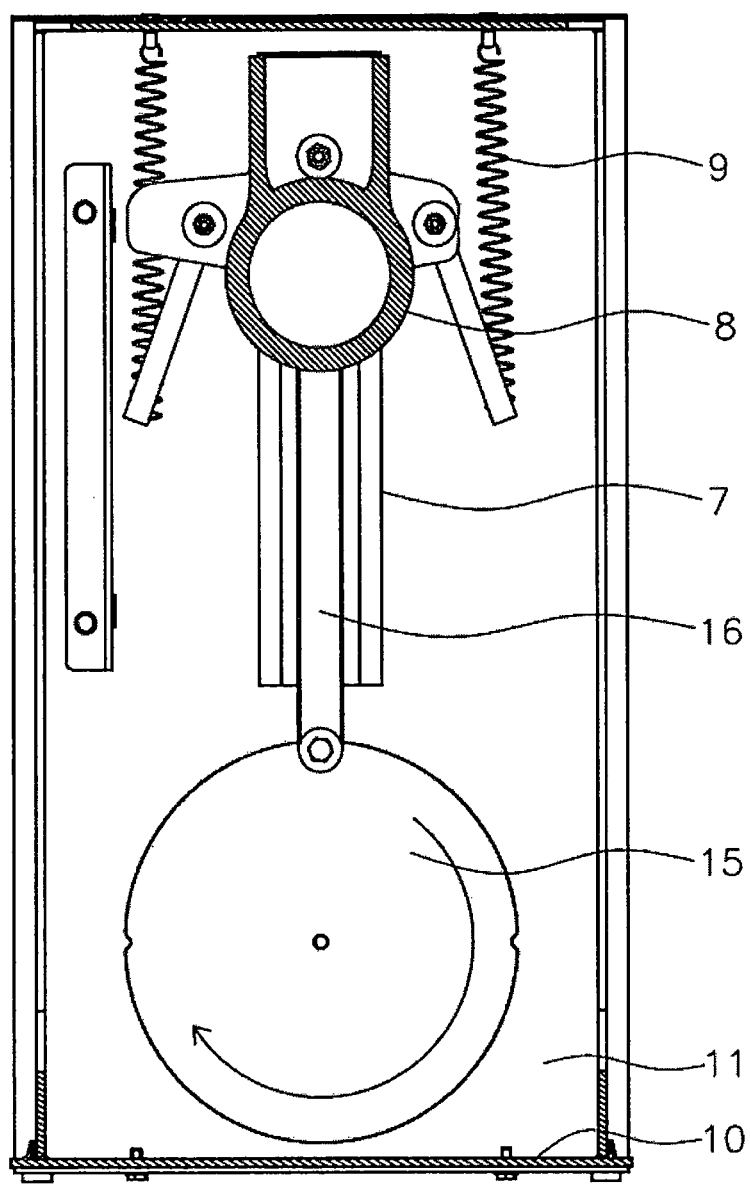
FIGS. 5 and 6 shows a cross-section made between the contrast observation chamber and the wall of the framework of the device, according to an embodiment of the means for moving the mentioned reflective surface, showing the open and closed positions, respectively.
Figure 6:
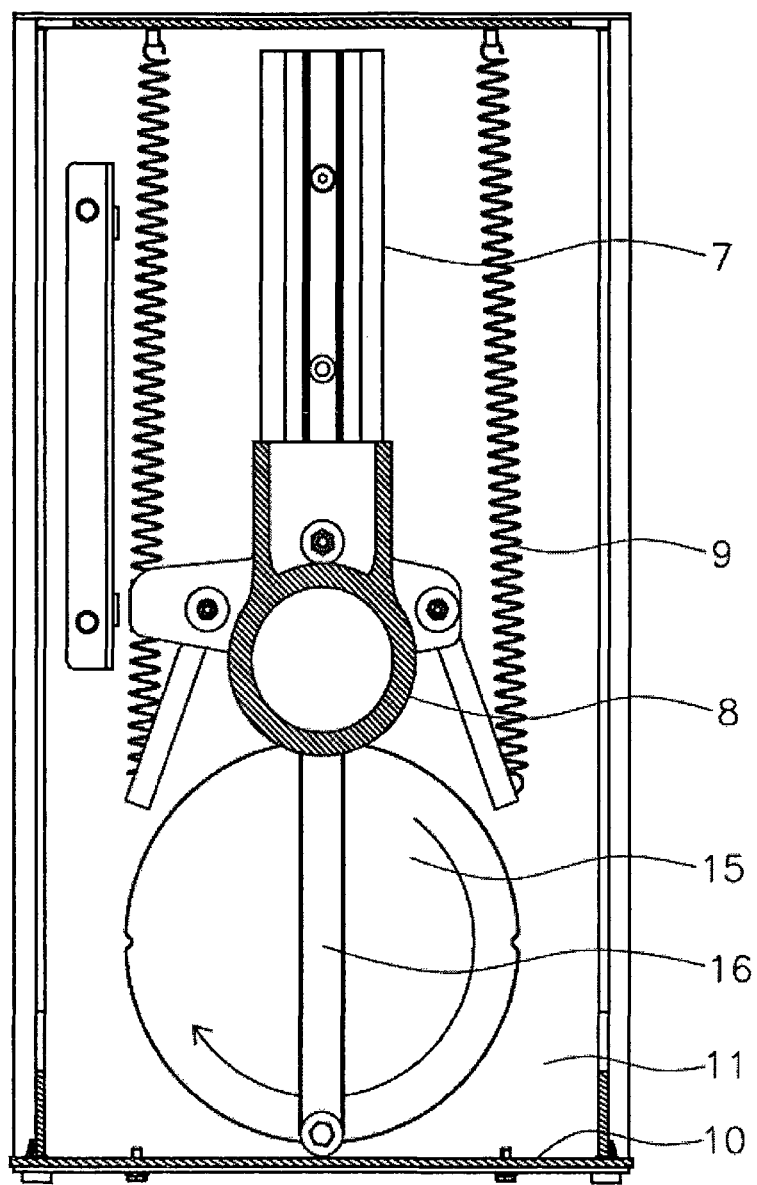

The mentioned wall 11 holds, suspended over the support 1 by means of an arm 13, a first screen 21 in the shape of a hollow spherical cap, shown in FIGS. 1 and 4, the maximum diameter of which is, in the present embodiment, greater than the diameter of the annular light emitting source 2. Said first screen 21 is a portion of a non-reflective surface 5, and has a hole in the center thereof through which an image capturing device 4 focuses on the support 1, which allow capturing overhead images of a culture dish located on said support 1.

It will be understood that a non-reflective surface 5 is a surface with a surface finish reflecting only a small part of the incident light, for example, having a black-colored matt surface finish, the albedo of which can be less than 0.2.

A second screen 22 with a hollow spherical geometry truncated at its two upper and lower poles is arranged covering the distance existing between the first screen 21 and the upper end of the pedestal 12, where the support 1 is located, the upper truncation coinciding with the maximum diameter of the spherical cap of the first screen 21, the assembly of the first screen 21 and the second screen 22 defining a contrast observation chamber 6 closed from the outside, preventing external light from entering in the closed position.

The diameter of the lower truncation of the second screen 22 is about the same as the diameter of the pedestal 12, the annular light emitting source 2 and the support 1 therefore being inscribed within said truncation, and therefore housed within the mentioned contrast observation chamber 6.

The mentioned second screen 22 has an upper portion also with a non-reflective surface finish, so said upper portion also forms part of the non-reflective surface 5 and continues the inner surface of the screen 21. The rest of the second screen 22 is a reflective surface 3, with a white- or metallic-colored surface finish with a high albedo, preferably greater than 0.8.

This distribution of the non-reflective surface 5 and reflective surface 3 on the inner face of a spherical contrast observation chamber 6 provides an optimal light diffusion on the support 1, while at the same time prevents light beams from hitting said support 1 in a approximately perpendicular direction, thereby assuring a tangent illumination that does not produce reflections or glare when capturing images of a culture dish deposited on said support 1.

To allow easy access and quick manipulation or replacement of the culture dish, it is proposed that the second screen 22 is attached on the outside thereof to guide means 7, 8 envisaged on the previously mentioned wall 11 of the framework which is erected perpendicular to the support 1. The guide means 7, 8 consist of vertical rails 8 on which a runner 7 attached to the second screen 22 slides. This movement allows lifting said second screen 22, its lower truncation being moved away from the pedestal 12, and the first screen 21 being housed inside the second screen 22. This open position allows free access to the support 1 so that a user can introduce or replace a culture dish on the support 1.

To achieve the movement of said second screen 22 it is proposed that spring means 9, made up of two vertical springs fixed at one end to the wall 11 of the framework, and at the other end to the runner 7 which is attached to the second screen 22, being said spring means 9 tared for counteracting the weight of the second screen 22, so only a small force is needed for the vertical movement of the second screen 22.

In this embodiment, said force for causing the movement of the second screen is provided by drive means consisting of a rotor 15 and a connecting rod 16, said rotor 15 being operated by means of a motor and articulated at its center with respect to the wall 11 of the framework, and said connecting rod 16 having an end attached in an articulated manner to said rotor 15, and another opposite end attached in an articulated manner to the runner 7 of the second screen 22. This mechanism causes the rotation of the rotor 15 to result in a linear movement of the runner 7 along the rails 8, the second screen 22 moving vertically, allowing it to change position from the closed position to the open position.

The operation of the device is as follows: the annular light emitting source 2 is switched on in a closed position of the screen 22, said light being reflected on the reflective surface 3 illuminating the entire surface of a culture dish located on the support 1 in a tangential, subtle and homogeneous manner, digital images of said culture dish are then taken by means of the image capturing device 4 for the automatic analysis of said images by means of a microcontroller integrated in the device running an algorithm which allows counting the colonies of bacteria existing on said culture dish. The information acquired by the device can be sent, for example, wirelessly to a portable computing device, such as a tablet or a mobile telephone. Alternatively, it has been envisaged that the device only acquires the images and that these images are transferred outwardly to an image processing device for counting the colonies. It is also contemplated that said image processing equipment is external, or even remote, to the device, the images being transmitted through cable or by means of a wireless communication device integrated in the proposed device for obtaining culture images, said wireless communication device being able to be a radio wave transmitter, such as for example, a WIFI antenna, a BLUETOOTH antenna, or any other communication protocol.

The invention claimed is:

1. A device for obtaining images of bacterial cultures in a dish, including:
   a support for culture dishes;
   at least one annular light emitting source arranged around said support for culture dishes, the light emitted by said source being oriented in a direction not hitting said support for culture dishes;
   at least one reflective surface arranged facing said at least one light emitting source for reflecting said light towards the support for culture dishes, and
   a centered image capturing device, facing and spaced from said support for culture dishes, for capturing images of a culture dish deposited on said support for culture dishes;
   wherein
      the mentioned at least one reflective surface, in combination with a non-reflective surface, form a contrast observation chamber, in which a culture dish arranged on the support for culture dishes is confined, the annular light emitting source and the centered image capturing device being integrated inside said observation chamber, and
      said non-reflective surface is arranged in an annular manner around the centered image capturing device, superposed with respect to the support for culture dishes and facing and spaced from the support for culture dishes, said non-reflective surface being provided with a surface finish with an albedo less than 0.4.

2. The device according to claim 1, wherein the reflective surface and/or the non-reflective surface have the geometry of a hollow spherical portion.

3. The device according to claim 2, wherein said reflective surface has at least one of its two poles truncated a diameter greater than the diameter of said at least one annular light emitting source.

4. The device according to claim 1, wherein the non-reflective surface has the geometry of a hollow spherical cap truncated a diameter greater than the diameter of said at least one annular light emitting source.

5. The device according to claim 1, wherein at least part of the reflective surface, or at least part of the reflective surface together with at least part of the non-reflective surface, is movable from a closed position surrounding said support, in which images of a culture dish can be obtained with optimum illumination conditions, and an open position, in which an access is offered for introducing culture dishes in the observation chamber.

6. The device according to claim 5, wherein at least part of the reflective surface, or at least part of the reflective surface together with at least part of the non-reflective surface, is movable in a direction perpendicular to the support for culture dishes, from a closed position surrounding said support, in which images of a culture dish can be obtained with optimum illumination conditions, and an open position raised above said support, in which an access is offered for introducing culture dishes in the contrast observation chamber.

7. The device according to claim 5, wherein the movable part of the contrast observation chamber is attached to guide means which allow its movement and limit its travel by drive means consisting of a rotor and a connecting rod.

8. The device according to claim 7, wherein at least one spring means counteracting the weight of said movable part of the contrast observation chamber in said open position has been envisaged.

9. The device according to claim 1, wherein the support for culture dishes is transparent.

10. The device according to claim 1, wherein the non-reflective surface has a size greater than the support for culture dishes, only the mentioned non-reflective surface and the centered image capturing device being superposed with respect to the support for culture dishes.

11. The device according to claim 1, wherein the non-reflective surface has a diameter greater than the annular light emitting source.

12. The device according to claim 1, wherein the reflective surface has a surface finish with an albedo greater than 0.6.

13. The device according to claim 1, wherein said centered image capturing device is a high-resolution digital photographic camera.

14. The device according to claim 1, wherein the device includes image processing equipment with a microcontroller running an algorithm for counting colonies of any color and/or measuring zones of inhibition of said observed bacterial cultures.

15. The device according to claim 1, wherein the device includes a wireless communication device transmitting the obtained images of the cultures to remote image processing equipment, provided with a microcontroller running an algorithm for counting colonies of any color and/or measuring zones of inhibition of said observed cultures.

16. The device according to claim 6, wherein the movable part of the contrast observation chamber is attached to guide means which allow its movement and limit its travel by drive means consisting of a rotor and a connecting rod.

17. The device according to claim 16, wherein the device further includes at least one spring means counteracting the weight of said movable part of the contrast observation chamber in said open position.

* * * * *